April 26, 1955 H. C. SWIM Plant Pat. 1,385
ROSE PLANT
Filed Aug. 23, 1954
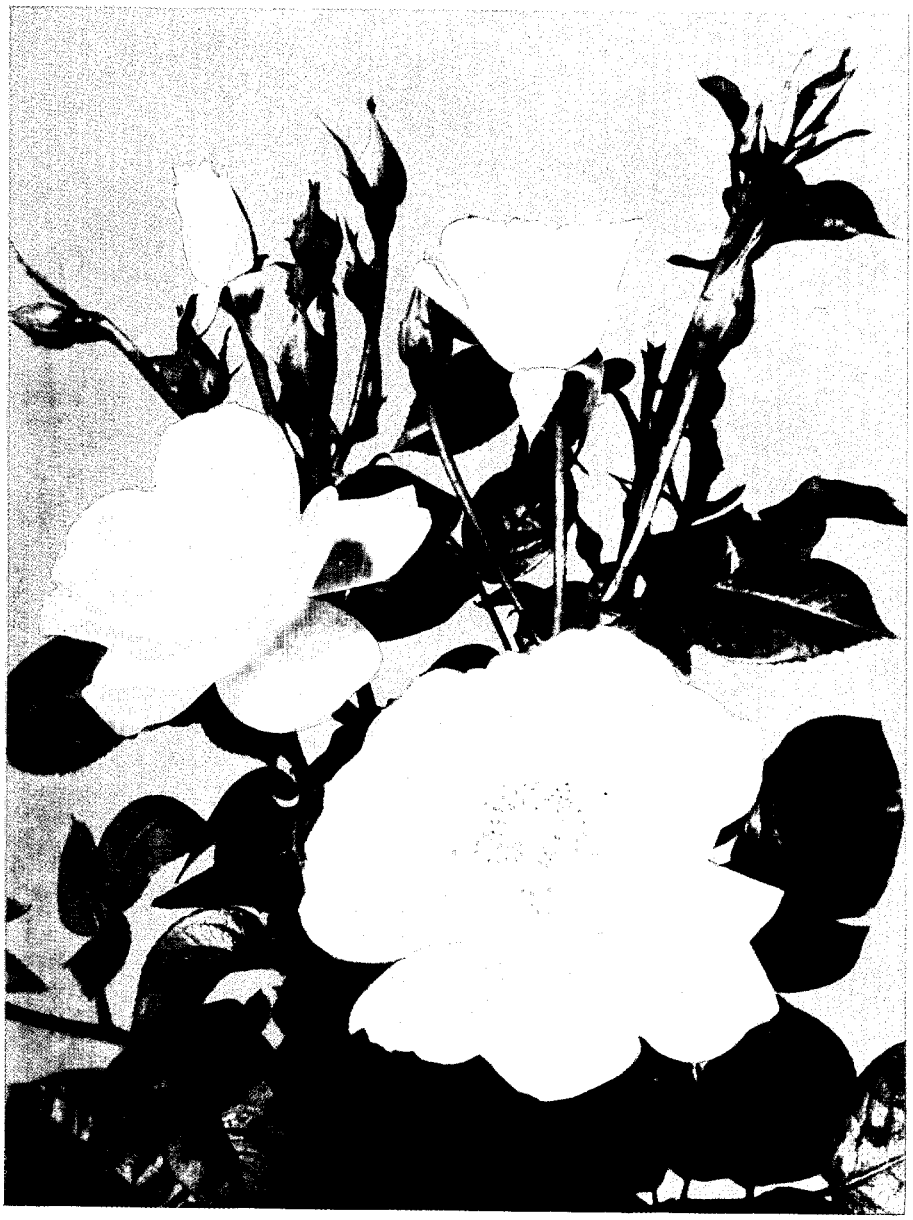
Inventor.
H. C. Swim
By: Robb & Robb
Attorneys.

United States Patent Office

Plant Pat. 1,385

Patented Apr. 26, 1955

1,385

ROSE PLANT

Herbert C. Swim, Ontario, Calif., assignor to Armstrong Nurseries, Inc., Ontario, Calif., a corporation of California Application August 23, 1954, Serial No. 451,727

1 Claim. (Cl. 47—61)

The present invention relates to a new and distinct variety of rose plant of the hybrid polyantha class, which was originated by me by crossing the variety "Fandango" (Plant Patent No. 894) with the variety "Pinocchio" (Plant Patent No. 484), the former constituting the seed parent, and the latter constituting the pollen parent.

The primary objective in making this cross was to produce a new rose variety which combines the most desirable characteristics of the parent varieties, thereby attaining a new and desirable combination of characteristics which have never heretofore been available in roses of this class. This objective was fully achieved, as evidenced by the fact that the new variety is particularly characterized by its abundant foliage, as inherited from its parent "Fandango," a cluster-blooming habit, inherited from the variety "Pinocchio," relatively large blooms approaching the size of the blooms of "Fandango," and a distinctive bloom color which is somewhat different from that of both parents, and which in general is Orange Red on the upper surface of the petals, with Yellow on the reverse surface, as transmitted from recessive genes contributed by both parents.

In comparison with its seed parent "Fandango," the bloom color of the new variety is Orange Red on the upper surface of the petals, but Yellow on the reverse surface, whereas the bloom color of "Fandango" is a medium shade of red, best described as Cherry Red, and the blooms of the new variety are produced in many-flowered clusters, whereas those of this parent are usually produced singly, or occasionally two or three to the stem.

As compared with its pollen parent "Pinocchio," the bloom color of my new variety is bi-colored as aforementioned, whereas the bloom color of "Pinocchio" is best described as Pink-suffused Salmon; the blooms of the new variety are larger in size than those of "Pinocchio," measuring from three to four inches in diameter, whereas those of "Pinocchio" measure only approximately two inches in diameter; and the foliage of the new variety is abundant and covers the plant well, whereas that of "Pinocchio" is less abundant and does not cover the plant as completely.

Asexual reproduction of my new variety by budding, as performed at Ontario, California, shows that the foregoing characteristics and distinctions come true to form and are established and transmitted through succeeding propagations.

The accompanying drawing shows typical specimens of the flowers, foliage and stems of my new variety in different stages of development, and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for garden decoration.
Class: Hybrid polyantha.
Breeding: Seedling.
*Seed parent.*—"Fandango."
*Pollen parent.*—"Pinocchio."
Propagation: Holds its distinguishing characteristics through succeeding propagations by budding.

FLOWER

Locality where grown and observed: Ontario, California.

Flowers borne: Usually several to stem; in regular, somewhat rounded clusters; on stems of normal strength and medium length.
Quantity of bloom: Abundant, outdoors.
Continuity: Continuous during growing season.
Fragrance: Moderate. Nature—spicy.
Bud:
*Peduncle.*—From average length to long; average caliper; erect; moderately smooth; numerous gland-tipped cilia; few prickles. Color—between Deep Chrysolite Green, Plate XXXI (Ridgwey) and Absinthe Green, Plate XXXI (Ridgway), overlaid with near Indian Red, Plate XXVII (Ridgway) on side exposed to sun.
*Before calyx breaks.*—Size—medium. Form—medium length; from pointed to ovoid; with foliaceous appendages and some gland-tipped cilia on the surface of the bud; usually without much-cut foliaceous parts extending beyond the tip of the bud.
*As calyx breaks.*—Color—between Aureolin, Plate 3/1, page 3 (Wilson) and Lemon Yellow, Plate 4/2, page 4 (Wilson), heavily overlaid with between Mandarin Red, Plate 17/2, page 17 (Wilson) and Vermillion, Plate 18/2, page 18 (Wilson), and sometimes marked with between Scarlet, Plate 19/1, page 19 (Wilson) and Geranium Lake, Plate 20/1, page 20 (Wilson).
*Sepals.*—Inner surface has fine, woolly tomentum; margins of alternate sepals lined with fine, woolly tomentum; others lined with gland-tipped cilia.
*As first petal opens.*—Size—average. Form—medium length; urn-shaped. Color: Outside—between Aureolin, Plate 3/2, page 3 (Wilson) and Lemon Yellow, Plate 4/2, page 4 (Wilson), overlaid with between Mandarin Red, Plate 17/2, page 17 (Wilson) and Vermillion, Plate 18/2, page 18 (Wilson), and sometimes marked with between Geranium Lake, Plate 20/1, page 20 (Wilson) and Carmine, Plate 21/1, page 21 (Wilson). Inside—between Scarlet, Plate 19, page 19 (Wilson) and Geranium Lake, Plate 20/1, page 20 (Wilson); inner surface of outermost petals somtimes fading to between Geranium Lake, Plate 20/2, page 20 (Wilson) and Carmine, Plate 21/1, page 21 (Wilson); small area at base of petal near attachment between Aureolin, Plate 3/1, page 3 (Wilson) and Lemon Yellow, Plate 4/1, page 4 (Wilson).
*Opening.*—Opens up well; is not retarded from opening by cold, hot, wet or dry weather.
Bloom:
*Size (when fully open).*—Large; from 3 inches to 4 inches.
*Petalage.*—Semi-double; from 20 to 30 petals, plus 5 to 10 petaloids; arranged regularly.
*Form.*—Flat-cupped at first, but becoming open later; petals being at first cupped, with lateral margins usually reflexed slightly about ¼ of upper portion of the petal, and lateral margins of outer petals often reflexed ½ or more of petal length, with apex sometimes reflected slightly about ⅛ of length of petal, and apex of outer petals sometimes reflexed ¼ of length of petal; becoming later at maturity flat-cupped, with lateral margins usually reflexed about ¼ to ⅓ of upper portion of petal, and lateral margins of outer petals usually reflexed ½ or more of petal length, with apex sometimes reflected ¼ or more of petal length.
Petals:
*Texture.*—From medium to thick; with inside satiny and outside from slightly shiny to satiny.
*Shape.*—Outside—broadly obovate, with apex flat, and rarely with 1 or 2 notches. Intermediate—obovate, with apex from rounded to flat, and rarely with 1 or 2 notches. Inside—narrowly obovate, with apex rounded, and sometimes with 1 or 2 notches.

This description of a newly opened flower was made from a rose grown outdoors in the month of May, at Ontario, California:

Color:

*Outside petal.*—Outside surface—between Aureolin, Plate 3/3, page 3 (Wilson) and Lemon Yellow, Plate 4/3, page 4 (Wilson), overlaid somewhat with between Scarlet, Plate 19/2, page 19 (Wilson) and Geranium Lake, Plate 20/3, page 20 (Wilson), and sometimes marked with between Carmine, Plate 21/1, page 21 (Wilson) and Crimson, Plate 22/2, page 22 (Wilson); small area at base of petal near attachment between Aureolin, Plate 3/2, page 3 (Wilson) and Lemon Yellow, Plate 4/2, page 4 (Wilson). Inside surface—between Geranium Lake, Plate 20/1, page 20 (Wilson) and Carmine, Plate 21/1, page 21 (Wilson); small area at base of petal near attachment between Aureolin, Plate 3/1, page 3 (Wilson) and Lemon Yellow, Plate 4/1, page 4 (Wilson).

*Intermediate petal.*—Outside surface—between Aureolin, Plate 3/3, page 3 (Wilson) and Lemon Yellow, Plate 4/3, page 4 (Wilson), overlaid somewhat with between Scarlet, Plate 19/2, page 19 (Wilson) and Geranium Lake, Plate 20/3, page 20 (Wilson); small area at base of petal near attachment between Aureolin, Plate 3/2, page 3 (Wilson) and Lemon Yellow, Plate 4/2, page 4 (Wilson). Inside surface—between Scarlet, Plate 19/1, page 19 (Wilson) and Geranium Lake, Plate 20/2, page 20 (Wilson); small area at base of petal near attachment between Aureolin, Plate 3/1, page 3 (Wilson) and Lemon Yellow, Plate 4/1, page 4 (Wilson).

*Inner petal.*—Outside surface—between Aureolin, Plate 3/3, page 3 (Wilson) and Lemon Yellow, Plate 4/3, page 4 (Wilson), overlaid somewhat with between Scarlet, Plate 19/2, page 19 (Wilson) and Geranium Lake, Plate 20/3, page 20 (Wilson); small area at base of petal near attachment between Aureolin, Plate 3/2, page 3 (Wilson) and Lemon Yellow, Plate 4/2, page 4 (Wilson). Inside surface—between Scarlet, Plate 19/1, page 19 (Wilson) and Geranium Lake, Plate 20/2, page 20 (Wilson); small area at base of petal near attachment between Aureolin, Plate 3/1, page 3 (Wilson) and Lemon Yellow, Plate 4/1, page 4 (Wilson).

This description was made from a rose that was open for 3 days outdoors in the month of May, at Ontario, California:

Color:

*Outside petal.*—Outside surface—between Rose Madder, Plate 23/3, page 23 (Wilson) and Tyrian Rose, Plate 24/3, page 24 (Wilson); small area at base of petal near attachment near Aureolin, Plate 3/2, page 3 (Wilson). Inside surface—between Crimson, Plate 22/2, page 22 (Wilson) and Rose Madder, Plate 23/2, page 23 (Wilson); small area at base of petal near attachment near Aureolin, Plate 3/2, page 3 (Wilson).

*Inside petal.*—Outside surface—between Rose Madder, Plate 23/3, page 23 (Wilson) and Tyrian Rose, Plate 24/3, page 24 (Wilson); small area at base of petal near attachment near Aureolin, Plate 3/2, page 3 (Wilson). Inside surface—between Crimson, Plate 22/2, page 22 (Wilson) and Rose Madder, Plate 23/2, page 23 (Wilson); small area at base of petal near attachment near Aureolin, Plate 3/2, page 3 (Wilson).

General color effect:

*Newly opened flower.*—Between Scarlet, Plate 19/1, page 19 (Wilson) and Geranium Lake, Plate 20/2, page 20 (Wilson); small area at base of petal near attachment between Aureolin, Plate 3/1, page 3 (Wilson) and Lemon Yellow, Plate 4/1, page 4 (Wilson).

*3-days open.*—Between Crimson, Plate 22/3, page 22 (Wilson) and Rose Madder, Plate 23/3, page 23 (Wilson); small area at base of petal near attachment near Aureolin, Plate 3/2, page 3 (Wilson).

Behavior: Drop off cleanly; not particularly affected by cold, hot, wet or dry weather.

Flower longevity: On bush in garden—4 days in May. Cut roses grown outdoors and kept at living-room temperatures—3 or 4 days in May.

REPRODUCTIVE ORGANS

Stamens: From average number to many; arranged regularly about pistils.

Filaments: From medium length to long; from 8 to 15 mm. in length; most with anthers.

*Color.*—Between Lemon Yellow, Plate 4/1, page 4 (Wilson) and Buttercup Yellow, Plate 5/2, page 5 (Wilson).

Anthers: From medium to large size; all open approximately at once.

*Color.*—Upper side—margins between Indian Yellow, Plate 6/2, page 6 (Wilson) and Saffron Yellow, Plate 7/2, page 7 (Wilson); remainder between Aureolin, Plate 3/2, page 3 (Wilson) and Lemon Yellow, Plate 4/2, page 4 (Wilson). Under side—margins between Indian Yellow, Plate 6/2, page 6 (Wilson) and Saffron Yellow, Plate 7/2, page 7 (Wilson); remainder between Aureolin, Plate 3/2, page 3 (Wilson) and Lemon Yellow, Plate 4/2, page 4 (Wilson).

Pollen: Moderate abundance.

*Color.*—Between Buttercup Yellow, Plate 5/3, page 5 (Wilson) and Indian Yellow, Plate 6/2, page 6 (Wilson).

Pistils: Average number; approximately 60 in number.

Styles: Moderately even; average length; average caliper; columnar; from 5 to 8 mm. in length.

*Color.*—Between Sap Green, Plate 62/3, page 62 (Wilson) and Uranium Green, Plate 63/3, page 63 (Wilson), with upper ⅓ of style overlaid with near Carmine, Plate 21/1, page 21 (Wilson).

Stigma: Color—between Uranium Green, Plate 63/3, page 63 (Wilson) and Dresden Yellow, Plate 64/3, page 64 (Wilson).

Ovaries: Usually all enclosed in calyx, but a few protruding from calyx.

Hips: Short; globular; smooth; walls thick and fleshy.

*Color (mature).*—Between Tangerine Orange, Plate 9, page 9 (Wilson) and Orpiment Orange, Plate 10/1, page 10 (Wilson).

Sepals: Permanent; from medium length to long; recurved.

*Color.*—Inside—between Biscay Green, Plate XVII (Ridgway) and Bice Green, Plate XVII (Ridgway), masked by White woolly tomentum. Outside—between Biscay Green, Plate XVII (Ridgway) and Bice Green, Plate XVII (Ridgway).

Seeds: Few; medium size; from 2 to 4 in number.

PLANT

Foliage:

*Leaves.*—Compound of usually 5 to 7 leaflets; abundant; medium size; heavy; leathery; glossy.

*Leaflets.*—Shape—ovoid, with apex acute. Base—round. Margin—simply serrate.

*Color.*—Mature: Upper surface—between Forest Green, Plate XVII (Ridgway) and Deep Dull Yellow-Green, (1) Plate XXXII (Ridgway); under surface—near Light Elm Green, Plate XVII (Ridgway). Young: Upper surface—near Light Cress Green, Plate XXXI (Ridgway), overlaid somewhat with near Indian Red, Plate XXVII (Ridgway); under surface — between Kildare Green, Plate XXXI (Ridgway) and Absinthe Green, Plate XXXI (Ridgway), overlaid with near Mineral Red, Plate XXVII (Ridgeway).

*Rachis (the supporting stem of the compound leaf).*—Average size. Upper side—grooved; hairy; some stipitate glands on edges. Under side—moderately smooth, but prickly.

*Stipules.*—Medium length; medium width; with medium length points turning out at an angle of more than 45°.

*Disease resistance.*—Average resistance to mildew, as compared with other varieties grown under comparable cultural conditions at Ontario, California.

Growth:

*Habit.*—Bushy; upright; much-branched.

*Growth.*—Very vigorous.

*Canes.*—From medium caliper to heavy.

*Main stems.*—Color—between Oil Green, Plate V (Ridgway) and Spinach Green, Plate V (Ridgway). Large prickles—many; from medium length to long; hooked slightly downward; with long, narrow base. Color—between Wood Brown, Plate XL (Ridgway) and Light Drab, Plate XLVI (Ridgway). Small prickles—few. Color—near Wood Brown, Plate XL (Ridgway). Hairs—none.

*Branches.*—Color—between Biscay Green, Plate XVII (Ridgway) and Light Elm Green, Plate XVII (Ridgway). Large prickles—many; from medium length to long; hooked slightly downward; with long, narrow base. Color—between Cinnamon Brown, Plate XV (Ridgway) and Verona Brown, Plate XXIX (Ridgway). Small prickles—few. Color—between Cinnamon Brown, Plate XV (Ridgway) and Verona Brown, Plate XXIX (Ridgway). Hairs—none.

*New shoots.*—Color—between Courge Green, Plate XVII (Ridgway) and Biscay Green, Plate XVII (Ridgway), heavily overlaid with between Mineral Red, Plate XXVII (Ridgway) and Indian Red, Plate XXVI (Ridgway). Large prickles—many; from medium length to long; hooked slightly downward; with long, narrow base. Color—near Mineral Red, Plate XXVII (Ridgway). Small prickles—several. Color—near Mineral Red, Plate XXVII (Ridgway). Hairs—none.

I claim:

A new and distinct variety of rose plant of the hybrid polyantha class, substantially as herein shown and described, characterized particularly as to novelty by its good cluster blooming habit, abundant foliage, relatively large blooms and the distinctive color of its blooms, the petals of which have a general color tonality of Orange Red on their upper surface and Yellow on their reverse surface.

No references cited.